(12) United States Patent
Lee et al.

(10) Patent No.: US 8,842,944 B2
(45) Date of Patent: Sep. 23, 2014

(54) OPTICAL FIBER HYDROGEN SENSOR AND METHOD OF MEASURING HYDROGEN CONCENTRATION USING THE SAME

(75) Inventors: YongWook Lee, Busan (KR); Wook Jang, Busan (KR)

(73) Assignee: Pukyong National University Industry-University Cooperation Foundation, Busan (KR)

( * ) Notice: Subject to any disclaimer, the term of this patent is extended or adjusted under 35 U.S.C. 154(b) by 133 days.

(21) Appl. No.: 13/436,256

(22) Filed: Mar. 30, 2012

(65) Prior Publication Data

US 2013/0230271 A1    Sep. 5, 2013

(30) Foreign Application Priority Data

Mar. 5, 2012  (KR) .......................... 10-2012-0022506

(51) Int. Cl.
*G02B 6/00* (2006.01)
(52) U.S. Cl.
CPC ........................................ *G02B 6/00* (2013.01)
USPC ............................................................ 385/12
(58) Field of Classification Search
CPC .................................................... G02B 6/12138
USPC ............................................................. 385/12
See application file for complete search history.

(56) References Cited

U.S. PATENT DOCUMENTS

| | | | | |
|---|---|---|---|---|
| 5,828,059 A * | 10/1998 | Udd | .......................... | 250/227.18 |
| 7,764,379 B1 * | 7/2010 | McDermott | .................. | 356/437 |
| 7,792,392 B2 * | 9/2010 | Chen et al. | ....................... | 385/12 |
| 7,889,332 B2 * | 2/2011 | Omichi et al. | ................ | 356/73.1 |
| 8,073,293 B2 * | 12/2011 | Kersey et al. | .................... | 385/12 |
| 8,369,671 B2 * | 2/2013 | Xia et al. | ....................... | 385/123 |

* cited by examiner

*Primary Examiner* — Charlie Peng
(74) *Attorney, Agent, or Firm* — Saliwanchik, Lloyd & Eisenschenk

(57) ABSTRACT

An optical fiber hydrogen sensor and a method of measuring a hydrogen concentration are provided. The optical fiber hydrogen sensor may include a light source, a polarization beam splitter connected to the light source to split light from the light source into two polarization beams, a high-birefringence optical fiber connected to the polarization beam splitter and coated with a hydrogen reactant, and an optical spectrum analyzer connected to the polarization beam splitter to measure interference spectrum generated at the high-birefringence optical fiber.

11 Claims, 6 Drawing Sheets

OPTICAL FIBER HYDROGEN SENSOR AND METHOD OF MEASURING HYDROGEN CONCENTRATION USING THE SAME

CROSS-REFERENCE TO RELATED APPLICATION

This application claims the benefit under 35 U.S.C. §119 of Korean Patent Application No. 10-2012-0022506, filed Mar. 5, 2012, which is hereby incorporated by reference in its entirety.

BACKGROUND

1. Field

The disclosure relates to an optical fiber hydrogen sensor and a method of measuring a hydrogen concentration using the same.

2. Description of the Related Art

In general, sensors for detecting hydrogen leakage (hydrogen sensors) are used to detect when hydrogen is leaked from a hydrogen-fueled vehicle or a hydrogen energy station.

However, conventional semiconductor-based hydrogen detection sensors require electric power. Thus, when electric leakage or sparks are produced, the sensors may explode on reaction with leaked hydrogen.

In order to solve the above problems, there has been a great deal of research conducted to develop an optical hydrogen sensor. Optical fiber-based hydrogen sensors using optical fibers made of a glass material have advantages in that they are electrically safe, their signal propagation velocities are high, and it is possible to detect signals at a long distance.

An optical fiber Bragg grating and a long-period optical fiber grating have been largely used for the conventional optical fiber-based hydrogen sensors.

The optical fiber Bragg grating and long-period optical fiber grating have a property that their resonance wavelengths are changed when strain or heat is applied to the gratings. When hydrogen is leaked and exposed to an optical fiber grating deposited with a hydrogen reactant (for example, palladium (Pd)), the hydrogen reactant expands by reaction with hydrogen, thereby applying strain to the optical fiber grating. As a result, the resonance wavelengths of the optical fiber grating are shifted. In this case, a hydrogen concentration may be measured by measuring a wavelength shift on the spectrum. When a tungsten oxide ($WO_3$) is used as the hydrogen reactant, an exothermic reaction takes place on reaction of the hydrogen reactant with hydrogen. In this case, the resonance wavelengths of the optical fiber grating are shifted by means of the generated heat.

However, the conventional optical fiber grating-based hydrogen sensors have the following problems since the resonance wavelengths of the optical fiber grating are shifted by two physical variables such as temperature and strain. First, when palladium is used as the hydrogen reactant, a change in outside temperature during detection of hydrogen affects the resonance wavelengths of the optical fiber grating, which makes it difficult to determine a change in resonance wavelength due to volume expansion of the palladium. Meanwhile, when a tungsten oxide is used as the hydrogen reactant, and external strain is applied to the optical fiber grating in a longitudinal direction, it is difficult to identify only a change in resonance wavelength due to an exothermic reaction of the tungsten oxide. Also, since the optical fiber grating is manufactured with long-term irradiation with ultraviolet rays, it may be easily broken due to external stress applied on a transverse axis and it is cumbersome to manufacture.

BRIEF SUMMARY

Exemplary embodiments provide an optical fiber hydrogen sensor that is not affected by a change in external temperature, easy to manufacture and highly resistant to external stress, and a method of measuring a hydrogen concentration using the same.

According to an exemplary embodiment, an optical fiber hydrogen sensor includes a light source, polarization beam splitter connected to the light source to split light from the light source into two polarization beams, a high-birefringence optical fiber connected to the polarization beam splitter and coated with a hydrogen reactant, and an optical spectrum analyzer connected to the polarization beam splitter to measure interference spectrum generated by the high-birefringence optical fiber.

According to another exemplary embodiment, a method of measuring a hydrogen concentration using an optical fiber hydrogen sensor system including a light source, a polarization beam splitter, a high-birefringence optical fiber and an optical spectrum analyzer is provided. The method includes splitting light from the light source into two polarization beams at the polarization beam splitter, introducing hydrogen into the high-birefringence optical fiber coated with a hydrogen reactant, changing wavelength of interference spectrum generated through a polarization-diversity loop configuration by the split polarization beams by reaction of the high-birefringence optical fiber with hydrogen, and measuring the generated interference spectrum at the optical spectrum analyzer.

BRIEF DESCRIPTION OF THE DRAWINGS

Exemplary embodiments are described in further detail below with reference to the accompanying drawings. It should be understood that various aspects of the drawings may have been exaggerated for clarity.

DETAILED DESCRIPTION

Figure 1:
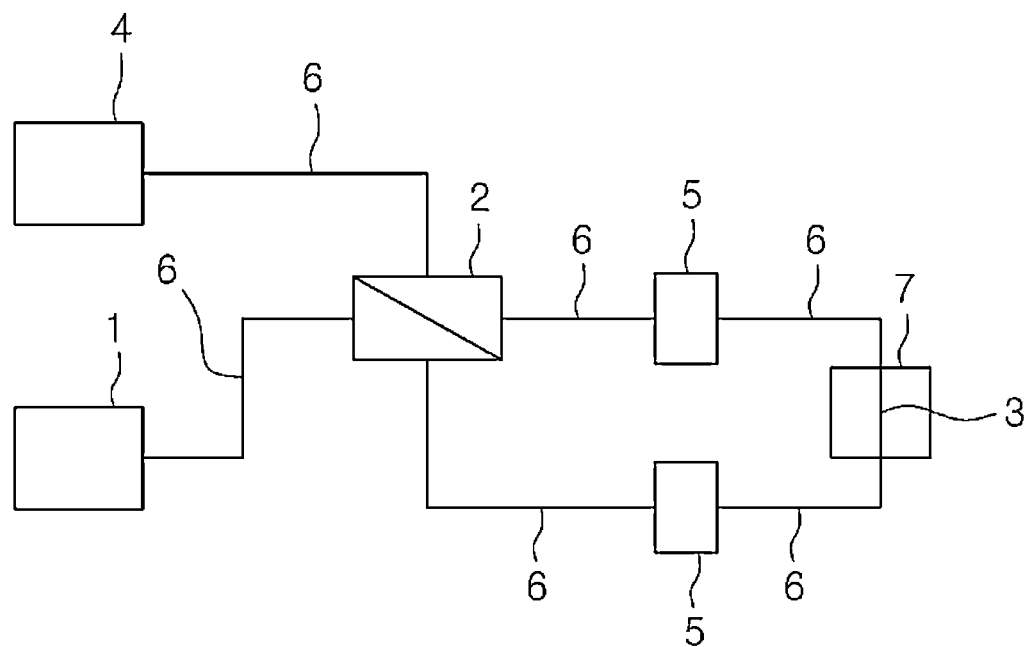
FIG. 1 is a schematic diagram of an optical fiber hydrogen sensor system according to one exemplary embodiment of the disclosure.

Various exemplary embodiments will now be described more fully with reference to the accompanying drawings in which some exemplary embodiments are shown. In the drawings, the thicknesses of layers and regions may be exaggerated for clarity. With reference to the appended drawings, exemplary embodiments of the disclosure will be described in detail below. To aid in understanding the disclosure, like numbers refer to like elements throughout the description of the figures, and the description of the same elements will be not reiterated.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

FIG. 1 is a schematic diagram of an optical fiber hydrogen sensor system according to one exemplary embodiment of the disclosure.

As shown in FIG. 1, the optical fiber hydrogen sensor system according to one exemplary embodiment of the disclosure includes a broadband source 1, a polarization beam splitter 2, a high-birefringence optical fiber 3, an optical spectrum analyzer 4, a polarization controller 5, a single-mode optical fiber 6 and a chamber 7.

The polarization beam splitter 2 is connected to the broadband source 1 to split light from the broadband source 1 into two polarization beams. In this case, the polarization beam splitter 2 may function to split light into two orthogonal polarization component beams.

The high-birefringence optical fiber 3 is connected to the polarization beam splitter 2 to generate interference spectrum. Light incident on the polarization beam splitter 2 is split into two polarization components. Then, a polarization-diversity loop configuration using optical paths of two beams is realized by crossing the light of the two split polarization components with each other and connecting the high-birefringence optical fiber 3 between the two split polarization components so that the light can return to the polarization beam splitter 2, and thus interference spectrum may be generated at an output terminal of the polarization beam splitter 2. A period of the interference spectrum is determined by the birefringence of the high-birefringence optical fiber 3. When the period of the interference spectrum is changed due to a change in birefringence of the high-birefringence optical fiber 3, an interference fringe appears to be shifted at a wavelength band.

The high-birefringence optical fiber 3 is an optical fiber having a high birefringence, and may include at least one selected from the group consisting of a panda-type polarization-maintaining optical fiber, a bow tie-type polarization-maintaining optical fiber, an elliptical core-type polarization-maintaining optical fiber, an elliptical cladding-type polarization-maintaining optical fiber and a polarization-maintaining photonic crystal optical fiber.

Meanwhile, the high-birefringence optical fiber 3 is coated with a hydrogen reactant. In this case, the hydrogen reactant may include at least one selected from the group consisting of Pd, tungsten (W), platinum (Pt), copper (Cu), zinc (Zn), chromium (Cr), zirconium (Zr), aluminum (Al), tin (Sn), manganese (Mn), nickel (Ni), germanium (Ge), titanium (Ti), vanadium (V), molybdenum (Mo), ruthenium (Ru), rhodium (Rh), rhenium (Re), calcium (Ca), yttrium (Y), lanthanum (La), cesium (Ce) or an oxide thereof.

A volume of the hydrogen reactant is changed by selective reaction only with hydrogen. In general, the hydrogen reactant such as Pd has a property of absorbing hydrogen, and thus a volume of the hydrogen reactant may expand at room temperature up to 900 times when the hydrogen reactant absorbs hydrogen. When the volume of the hydrogen reactant expands by reaction with hydrogen, the hydrogen reactant applies strain to the high-birefringence optical fiber 3 to cause a change in birefringence of the high-birefringence optical fiber 3. Thus, the hydrogen reactant may function as a transducer that shifts wavelength of the interference spectrum.

When the hydrogen reactant reacts with hydrogen, the hydrogen reactant coated on the high-birefringence optical fiber 3 expands. The birefringence of the high-birefringence optical fiber 3 is changed by the expanding hydrogen reactant. Then, the changed birefringence of the high-birefringence optical fiber 3 allows the high-birefringence optical fiber 3 to shift wavelength of interference spectrum generated through a polarization-diversity loop configuration.

The optical spectrum analyzer 4 is connected to an output terminal of the polarization beam splitter 2 to measure the interference spectrum generated by the high-birefringence optical fiber 3. In this case, the optical spectrum analyzer 4 may measure a hydrogen concentration by measuring a wavelength shift of the interference spectrum or a change in output power.

The polarization controller 5 is connected to the polarization beam splitter 2 to control the polarization state of light rotating within the polarization-diversity loop composed of the polarization beam splitter 2 and the high-birefringence optical fiber 3. The polarization controller 5 may be composed of a half-wave plate, a quarter-wave plate, or a combination of the half-wave plate and quarter-wave plate. Also, the polarization controller 5 may function to control the visibility of interference spectrum. The polarization controller 5 may improve the visibility of interference spectrum so that the wavelength displacement of shifting spectrum can be easily measured when the hydrogen reactant reacts with hydrogen.

The single-mode optical fiber 6 connects the broadband source 1, the polarization beam splitter 2, the high-birefringence optical fiber 3, the optical spectrum analyzer 4 and the polarization controller 5. The single-mode optical fiber 6 has a cut-off frequency below which light is guided in a single mode. Also, the single-mode optical fiber 6 may include at least one selected from the group consisting of a silica-based optical fiber, a fluorine-based optical fiber, a rare-earth element-based optical fiber, a polymer-based optical fiber and a flint glass optical fiber, depending on the kinds of materials. Also, the single-mode optical fiber 6 may include at least one selected from the group consisting of a polarization-maintaining optical fiber, a non-linear optical fiber, a dispersion-shifted optical fiber, a dispersion compensation optical fiber and a non-zero dispersion-shifted optical fiber, depending on optical properties.

The chamber 7 is configured so that the high-birefringence optical fiber 3 can be accommodated inside the chamber 7. This detailed description will be described later with reference to FIG. 3A.

Figure 2A:
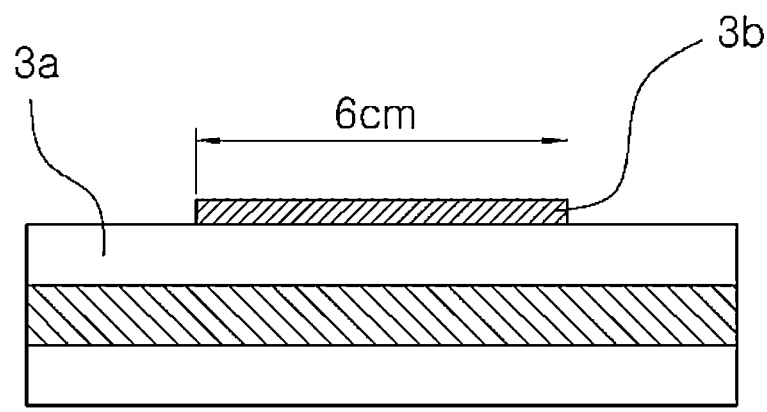
FIG. 2A is a side view of a high-birefringence optical fiber coated with a hydrogen reactant according to one exemplary embodiment of the disclosure.
Figure 2B:
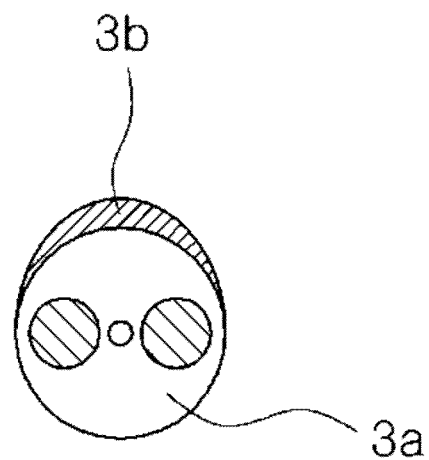
FIG. 2B is a cross-sectional view of a high-birefringence optical fiber coated with a hydrogen reactant.

FIG. 2A is a side view of a high-birefringence optical fiber coated with a hydrogen reactant according to one exemplary embodiment of the disclosure, and FIG. 2B is a cross-sectional view of a high-birefringence optical fiber coated with a hydrogen reactant.

Referring to FIGS. 2A and 2B, the high-birefringence optical fiber coated with a hydrogen reactant according to one exemplary embodiment of the disclosure includes an optical fiber body 3a and a hydrogen reactant 3b. According to one exemplary embodiment, the hydrogen reactant 3b may be coated to a length of 6 cm and a thickness of 400 nm after removing an acrylic coating of the optical fiber body 3a. When the hydrogen reactant 3b reacts with hydrogen, the hydrogen reactant 3b expands by absorbing hydrogen, thereby applying strain to the optical fiber body 3a. Such strain may act to shift a wavelength range of interference spectrum by changing a birefringence of the high-birefringence optical fiber 3.

Figure 3A:
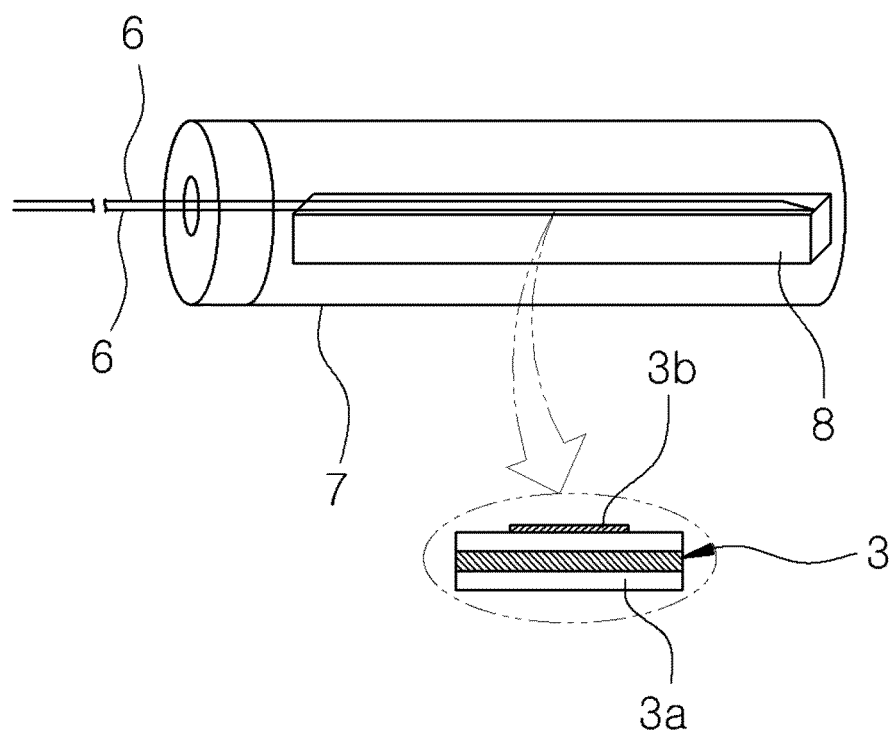
FIG. 3A is a mimetic diagram showing the inside of a chamber according to one exemplary embodiment of the disclosure.

FIG. 3A is a mimetic diagram showing the inside of a chamber according to one exemplary embodiment of the disclosure.

In FIG. 3A, the high-birefringence optical fiber 3 connected to the single-mode optical fiber 6 through fusion splicing is inserted into the chamber 7. Also, an auxiliary structure 8 may be mounted inside the chamber 7 to intercept external perturbation rather than effects of a hydrogen concentration. The auxiliary structure 8 may minimize an effect of a change in pressure in the chamber 7 on the high-birefringence optical fiber 3 since the auxiliary structure 8 functions to anchor the high-birefringence optical fiber 3.

Figure 3B:
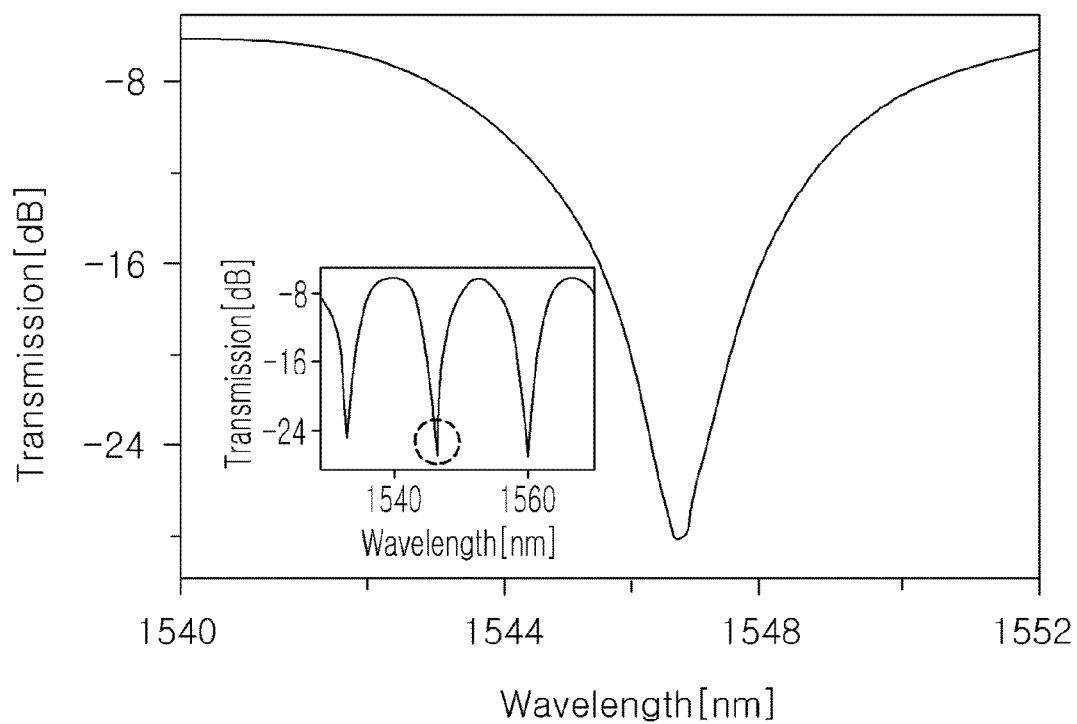
FIG. 3B is a diagram showing transmission spectrum measured at an optical spectrum analyzer according to one exemplary embodiment of the disclosure.

FIG. 3B is a diagram showing transmission spectrum measured at an optical spectrum analyzer according to one exemplary embodiment of the disclosure.

The transmission spectrum measured at the optical spectrum analyzer 4 are shown in FIG. 3B. Output interference spectrum measured at a wide wavelength range are shown in the small graph shown in FIG. 3B.

In order to measure a hydrogen concentration, first, the polarization controller 5 is adjusted to maximize the visibility of interference spectrum. Among valleys of interference spectrum, a valley close to 1546.85 nm is then used as a sensing indicator, as shown in FIG. 3B.

Since a hydrogen reactant reacts with hydrogen when the hydrogen is injected inside the chamber 7, wavelength of interference spectrum at the valley selected as the sensing indicator is shifted. The optical spectrum analyzer 4 may measure a hydrogen concentration by analyzing the displacement of such spectrum wavelengths.

Figure 4A:
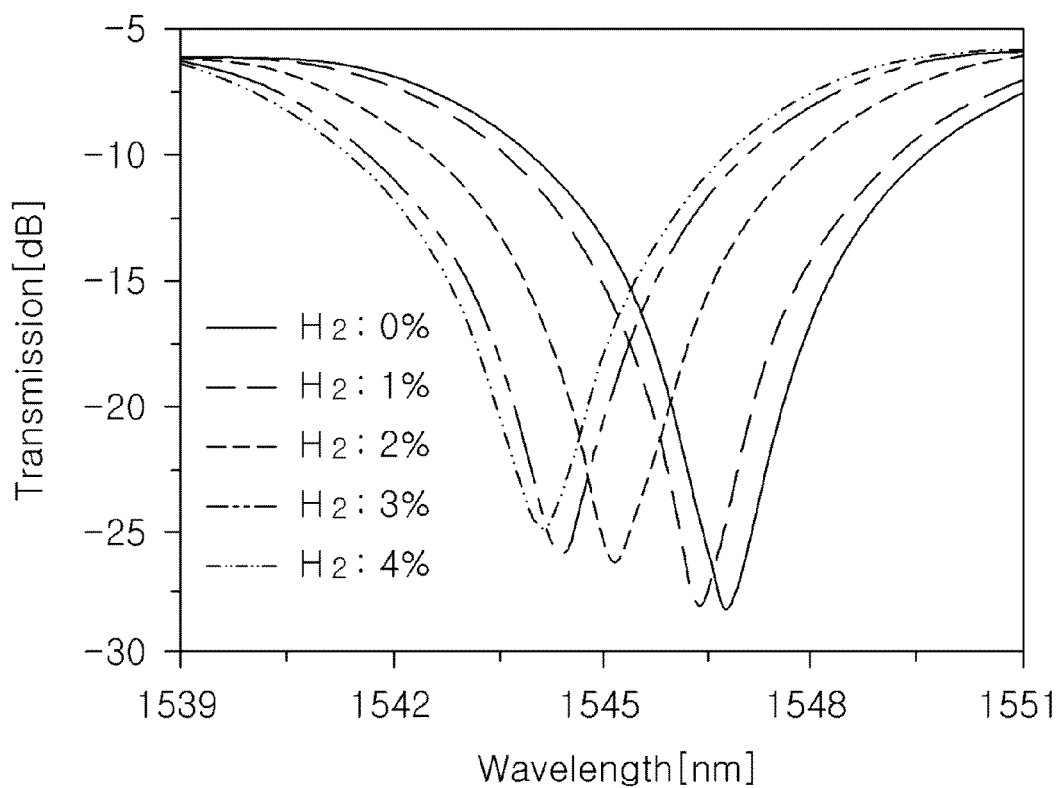
FIG. 4A is a diagram showing a change in transmission spectrum according to an injected hydrogen concentration at the valley selected as a sensing indicator.

FIG. 4A is a diagram showing a change in transmission spectrum according to an injected hydrogen concentration at the valley selected as a sensing indicator.

A pattern at which spectrum at the valley selected as the sensing indicator is shifted when an injected hydrogen concentration is changed from 1% to 4% is shown in FIG. 4A. The wavelength at the valley selected as the sensing indicator is shifted in a short wavelength direction with an increase in injected hydrogen concentration.

Figure 4B:
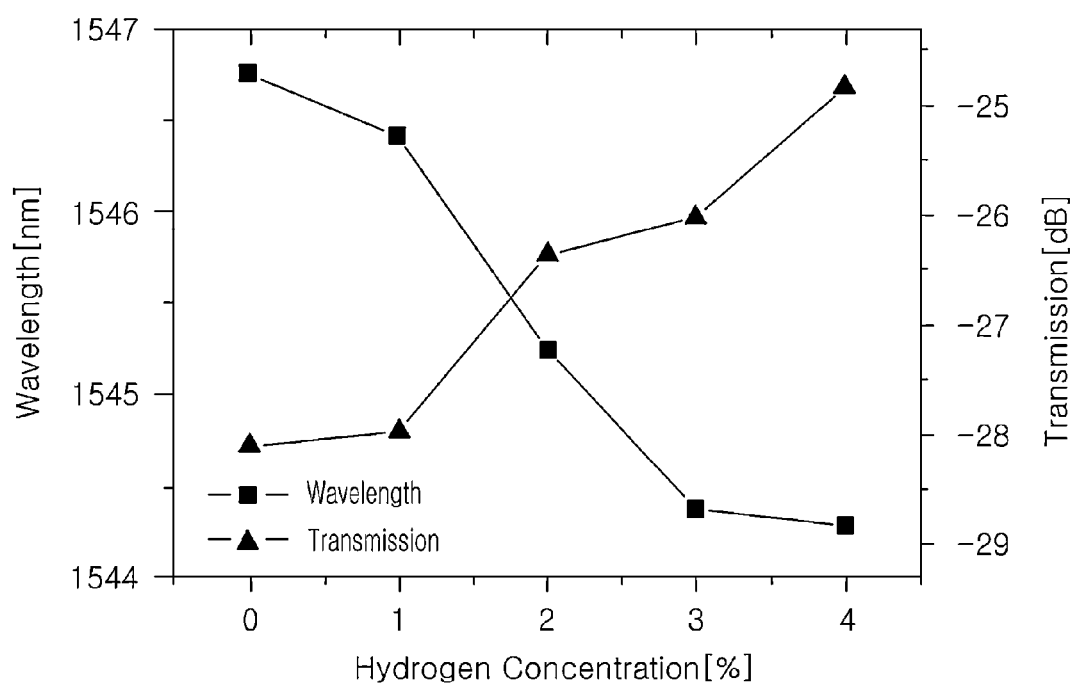
FIG. 4B is a diagram showing changes in wavelength displacement and transmittance according to a hydrogen concentration at the valley selected as a sensing indicator.

FIG. 4B is a diagram showing changes in wavelength displacement and transmission according to a hydrogen concentration at the valley selected as a sensing indicator.

Referring to FIG. 4B, when an injected hydrogen concentration is 1, 2, 3 and 4%, the wavelength displacements at the valley selected as the sensing indicator are approximately 0.40 nm, approximately 1.60 nm, approximately 2.46 nm and approximately 2.65 nm, respectively. As the injected hydrogen concentration increases, the wavelength at the valley tends to decrease. However, when the injected hydrogen concentration reaches 4%, the wavelength displacement is remarkably reduced. Also, when the injected hydrogen concentration is 1, 2, 3 and 4%, the transmission values at the valley selected as the sensing indicator are approximately 28.0 dB, approximately 26.4 dB, approximately 26.0 dB and approximately 24.8 dB, respectively. As the injected hydrogen concentration increases, the transmission at the valley tends to decrease.

Figure 5:
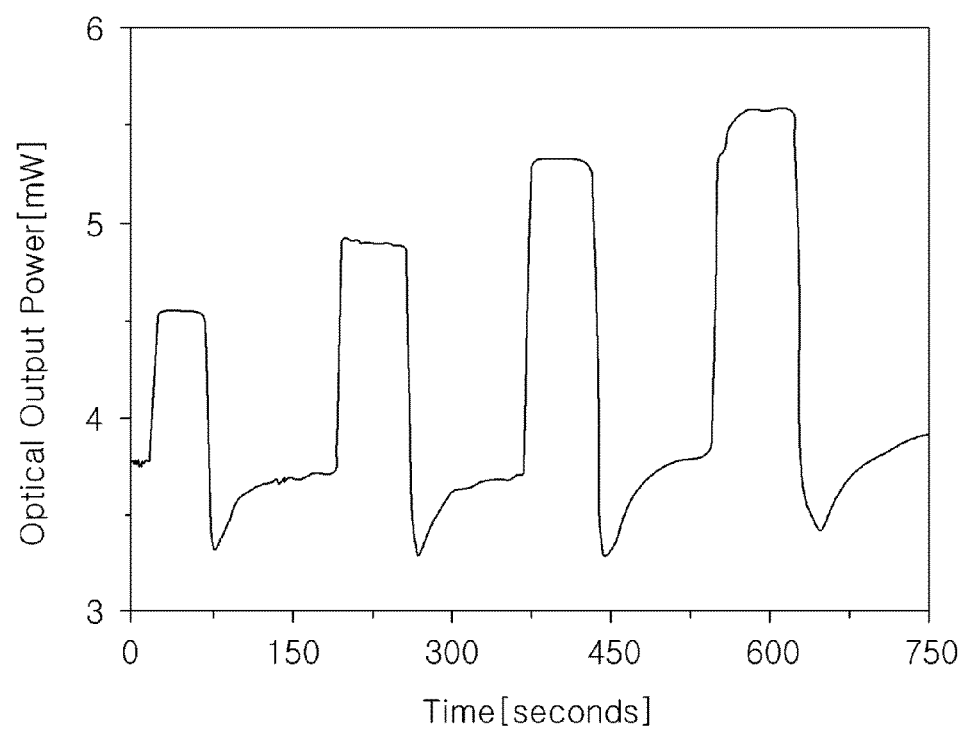
FIG. 5 is a diagram showing a change in optical power of a sensor output according to an injected hydrogen concentration using an optical powermeter.

FIG. 5 is a diagram showing a change in optical power of a sensor output according an injected hydrogen concentration using an optical powermeter.

The results obtained using an optical powermeter instead of the optical spectrum analyzer 4 so as to measure a reaction time of hydrogen in the optical fiber hydrogen sensor system are shown in FIG. 5. Referring to FIG. 5, four peaks represent optical output intensities and reaction times from the left in FIG. 5, as measured when a hydrogen concentration is 1, 2, 3 and 4%.

When the injected hydrogen concentration is 1, 2, 3 and 4%, the optical output intensities may be approximately 0.8 mW, approximately 1.1 mW, approximately 1.5 mW and approximately 1.8 mW, respectively. Also, the reaction time of a sensor output signal when hydrogen is injected into or discharged from the chamber 7 may be approximately 10 seconds, and the reaction time including stabilization time may be approximately 100 seconds.

Next, a method of measuring a hydrogen concentration according to one exemplary embodiment of the disclosure will be described.

Referring to FIG. 1, the optical fiber hydrogen sensor system includes a broadband source 1, a polarization beam splitter 2, a high-birefringence optical fiber 3 and an optical spectrum analyzer 4. In a method of measuring a hydrogen concentration using the optical fiber hydrogen sensor system, first, the polarization beam splitter 2 splits light from the broadband source 1 into two polarization components. In this case, the polarization beam splitter 2 may split light from the broadband source 1 into two orthogonal polarization component beams. The two split polarization components generate interference spectrum through a polarization-diversity loop configuration.

Next, hydrogen is introduced into the high-birefringence optical fiber 3 coated with a hydrogen reactant, and the hydrogen reactant coated on the high-birefringence optical fiber 3 expands by reaction with hydrogen. The expanding hydrogen reactant causes a change in birefringence of the high-birefringence optical fiber 3, and thus the changed birefringence of the high-birefringence optical fiber 3 shifts wavelength of the interference spectrum output from the optical fiber hydrogen sensor system.

Thereafter, the optical spectrum analyzer 4 measures the interference spectrum output from the optical fiber hydrogen sensor system. In this case, the optical spectrum analyzer 4 may measure a hydrogen concentration by measuring a wavelength shift of the interference spectrum or a change in output optical power.

According to one exemplary embodiment of the disclosure, the wavelength displacement of interference spectrum output from a sensor and a change in output optical power can be analyzed so that an injected hydrogen concentration can be measured and the exposure to hydrogen can be checked regardless of a change in outside temperature.

According to one exemplary embodiment of the disclosure, the optical fiber hydrogen sensor can also be easily fabricated, compared to that using a conventional optical fiber grating, and have improved sensitivity to the sensor output since the strain sensitivity of birefringence is higher than the strain sensitivity of the optical fiber grating.

According to one exemplary embodiment of the disclosure, the optical fiber hydrogen sensor can also be useful in saving the costs and time required to manufacture an optical fiber grating since the optical fiber hydrogen sensor does not require an optical fiber grating. Also, the optical fiber hydrogen sensor is highly resistant to external stress applied on a transverse axis, compared to the optical fiber grating-based hydrogen sensor.

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims.

What is claimed is:

1. An optical fiber hydrogen sensor comprising:
   a light source;
   a polarization beam splitter connected to the light source to split light from the light source into two polarization beams;
   a high-birefringence optical fiber connected to the polarization beam splitter and coated with a hydrogen reactant; and
   an optical spectrum analyzer connected to the polarization beam splitter to measure interference spectrum generated by the high-birefringence optical fiber.

2. The optical fiber hydrogen sensor according to claim 1, wherein the polarization beam splitter splits light from the light source into two orthogonal polarization component beams.

3. The optical fiber hydrogen sensor according to claim 1, wherein the high-birefringence optical fiber comprises at least one selected from the group consisting of a panda-type polarization-maintaining optical fiber, a bow tie-type polarization-maintaining optical fiber, an elliptical core-type polarization-maintaining optical fiber, an elliptical cladding-type polarization-maintaining optical fiber and a polarization-maintaining photonic crystal optical fiber.

4. The optical fiber hydrogen sensor according to claim 1, wherein the hydrogen reactant comprises at least one selected from the group consisting of palladium, tungsten, platinum, copper, zinc, chromium, zirconium, aluminum, tin, manganese, nickel, germanium, titanium, vanadium, molybdenum, ruthenium, rhodium, rhenium, calcium, yttrium, lanthanum, cesium or an oxide thereof.

5. The optical fiber hydrogen sensor according to claim 1, wherein the optical spectrum analyzer measures a hydrogen concentration by measuring a wavelength shift of the interference spectrum or a change in output optical power.

6. The optical fiber hydrogen sensor according to claim 1, wherein the optical fiber hydrogen sensor further comprises a polarization controller connected to the polarization beam splitter to control the polarization state of light rotating within a polarization-diversity loop composed of the polarization beam splitter and high-birefringence optical fiber.

7. The optical fiber hydrogen sensor according to claim 6, wherein the polarization controller is composed of a half-wave plate, a quarter-wave plate or a combination of the half-wave plate and quarter-wave plate.

8. A method of measuring a hydrogen concentration using an optical fiber hydrogen sensor system comprising a light source, a polarization beam splitter, a high-birefringence optical fiber and an optical spectrum analyzer, the method comprising:
   splitting light from the light source into two polarization beams at the polarization beam splitter;
   introducing hydrogen into the high-birefringence optical fiber coated with a hydrogen reactant;
   changing wavelength of interference spectrum generated through a polarization-diversity loop configuration by the split polarization beams by reaction of the high-birefringence optical fiber with hydrogen; and
   measuring the generated interference spectrum at the optical spectrum analyzer.

9. The method according to claim 8, wherein the splitting of the light into the two polarization beams is performed by splitting the light from the light source into two orthogonal polarization component beams.

10. The method according to claim 8, wherein the measuring of the interference spectrum is performed for measuring a hydrogen concentration by measuring a wavelength shift of the interference spectrum or a change in output optical power.

11. The method according to claim 8, wherein the changing of the wavelength of the interference spectrum further comprises:
   allowing the hydrogen reactant to expand when the hydrogen reactant reacts with hydrogen;
   changing a birefringence of the high-birefringence optical fiber by means of the expanded hydrogen reactant; and
   generating interference spectrum whose wavelength is changed to correspond to the changed birefringence of the high-birefringence optical fiber.

* * * * *